(12) United States Patent
LaStella

(10) Patent No.: US 7,427,505 B2
(45) Date of Patent: Sep. 23, 2008

(54) FECAL OCCULT BLOOD TESTING DEVICE AND METHOD

(75) Inventor: Vincent LaStella, Clark, NJ (US)

(73) Assignee: Immunostics, Inc., Ocean, NJ (US)

( * ) Notice: Subject to any disclaimer, the term of this patent is extended or adjusted under 35 U.S.C. 154(b) by 0 days.

(21) Appl. No.: 10/896,607

(22) Filed: Jul. 22, 2004

(65) Prior Publication Data
US 2006/0018789 A1    Jan. 26, 2006

(51) Int. Cl.
*G01N 33/48* (2006.01)

(52) U.S. Cl. .............................. 436/66; 422/58; 422/61

(58) Field of Classification Search ............. 422/56–61; 436/66
See application file for complete search history.

(56) References Cited

U.S. PATENT DOCUMENTS

| | | |
|---|---|---|
| 3,996,006 A | 12/1976 | Pagano |
| 4,092,120 A | 5/1978 | Suovaniemi et al. |
| 4,259,964 A | 4/1981 | Levine |
| 4,273,741 A | 6/1981 | Levine |
| 4,333,734 A | 6/1982 | Fleisher |
| 4,365,970 A * | 12/1982 | Lawrence et al. ............. 436/66 |
| 4,367,750 A | 1/1983 | Levine |
| 4,420,353 A | 12/1983 | Levine |
| 4,427,769 A | 1/1984 | Adlercreutz et al. |
| 4,486,536 A * | 12/1984 | Baker et al. ................... 436/66 |
| 4,559,949 A | 12/1985 | Levine |
| 4,615,982 A | 10/1986 | Lawrence |
| 4,645,743 A | 2/1987 | Baker et al. |
| 4,789,629 A * | 12/1988 | Baker et al. ................ 435/7.92 |
| 4,804,518 A | 2/1989 | Levine et al. |
| 4,808,379 A | 2/1989 | Wardlaw et al. |
| 4,818,702 A | 4/1989 | Lawrence |

(Continued)

FOREIGN PATENT DOCUMENTS

WO    WO 90/03927    4/1990

(Continued)

OTHER PUBLICATIONS

Allison, J, et al., A Comparison of Fecal Occult-Blood Tests for Colorectal-Cancer Screening, web publication on www.journalclub.org.

(Continued)

*Primary Examiner*—Lyle A Alexander
(74) *Attorney, Agent, or Firm*—Stroock & Stroock & Lavan LLP

(57) ABSTRACT

A specimen testing device having a first panel including a first aperture for receiving a first specimen and a second aperture for receiving a second specimen; a second panel; a sheet disposed between the first and second panels for receiving at least the first specimen through the first aperture, wherein the sheet includes a test area having a reagent for possible reaction to the first specimen as part of a primary test procedure; and a removable tab at least partially aligned with the second aperture for receiving the second specimen, the removable tab accessible from an exterior of the device and available for use in a secondary test procedure. A method of testing for the presence of blood in fecal matter including primary and secondary testing of the fecal matter. A test kit including a specimen testing device and reagents for performing a primary test a secondary test on specimens.

17 Claims, 9 Drawing Sheets

U.S. PATENT DOCUMENTS

| | | | |
|---|---|---|---|
| 4,820,646 A | 4/1989 | Lawrence | |
| 4,937,197 A | 6/1990 | Lawrence | |
| 4,939,097 A | 7/1990 | Lawrence | |
| 4,942,132 A | 7/1990 | Lawrence | |
| 4,971,914 A | 11/1990 | Lawrence | |
| 5,053,342 A | 10/1991 | Lawrence | |
| 5,064,766 A | 11/1991 | Wardlaw et al. | |
| 5,068,197 A | 11/1991 | Lawrence | |
| 5,094,956 A | 3/1992 | Grow et al. | |
| 5,100,619 A * | 3/1992 | Baker et al. | 422/58 |
| 5,106,582 A | 4/1992 | Baker | |
| 5,171,529 A | 12/1992 | Schreiber | |
| 5,192,501 A | 3/1993 | Guadagno et al. | |
| 5,196,167 A | 3/1993 | Guadagno et al. | |
| 5,198,365 A | 3/1993 | Grow et al. | |
| 5,215,713 A | 6/1993 | Steinbiss et al. | |
| 5,217,874 A | 6/1993 | Guadagno et al. | |
| 5,264,181 A * | 11/1993 | Schreiber | 422/58 |
| 5,310,680 A | 5/1994 | Baker et al. | |
| 5,391,498 A | 2/1995 | Baker et al. | |
| 5,447,868 A | 9/1995 | Augurt | |
| 5,563,071 A | 10/1996 | Augurt | |
| 5,702,913 A | 12/1997 | Guadagno | |
| 5,747,344 A | 5/1998 | Cleator | |
| 5,747,351 A | 5/1998 | Hemmati | |
| 5,948,687 A * | 9/1999 | Cleator | 436/66 |
| 6,221,678 B1 | 4/2001 | Chandler | |
| 6,271,046 B1 | 8/2001 | Chandler | |
| 6,410,336 B1 | 6/2002 | Augurt | |
| 6,436,714 B1 | 8/2002 | Clawson et al. | |

FOREIGN PATENT DOCUMENTS

| | | |
|---|---|---|
| WO | WO 90/13819 | 11/1990 |
| WO | WO 00/51029 | 9/2000 |
| WO | WO 00/54029 | 9/2000 |
| WO | WO02/080775 | 10/2002 |

OTHER PUBLICATIONS

Beg, M., et al., Occult Gastro-Intestinal Bleeding Detection, Interpretation, and Evaluation, web publication on www.indigene.com.

Website: www.insuretest.com.

* cited by examiner

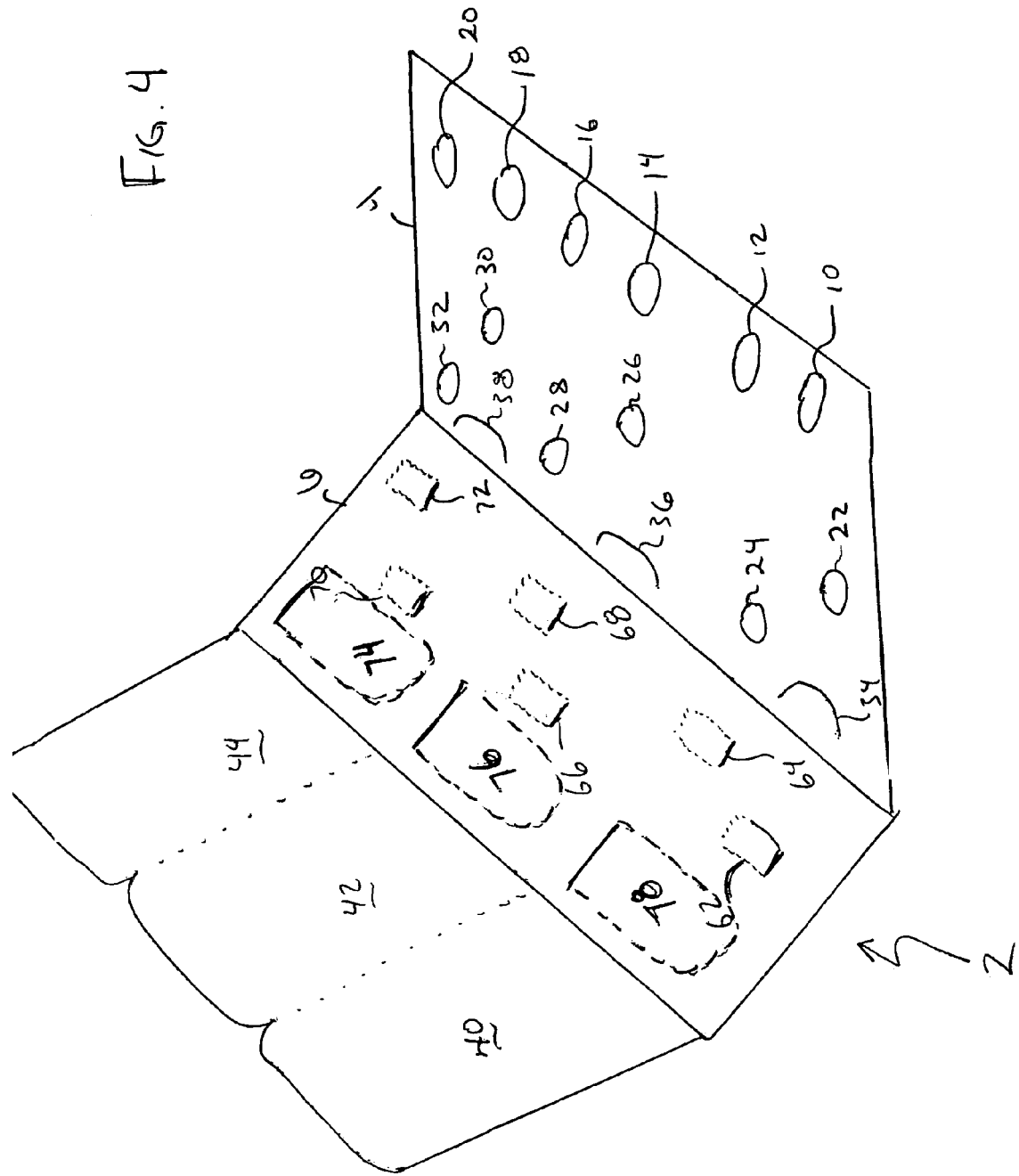

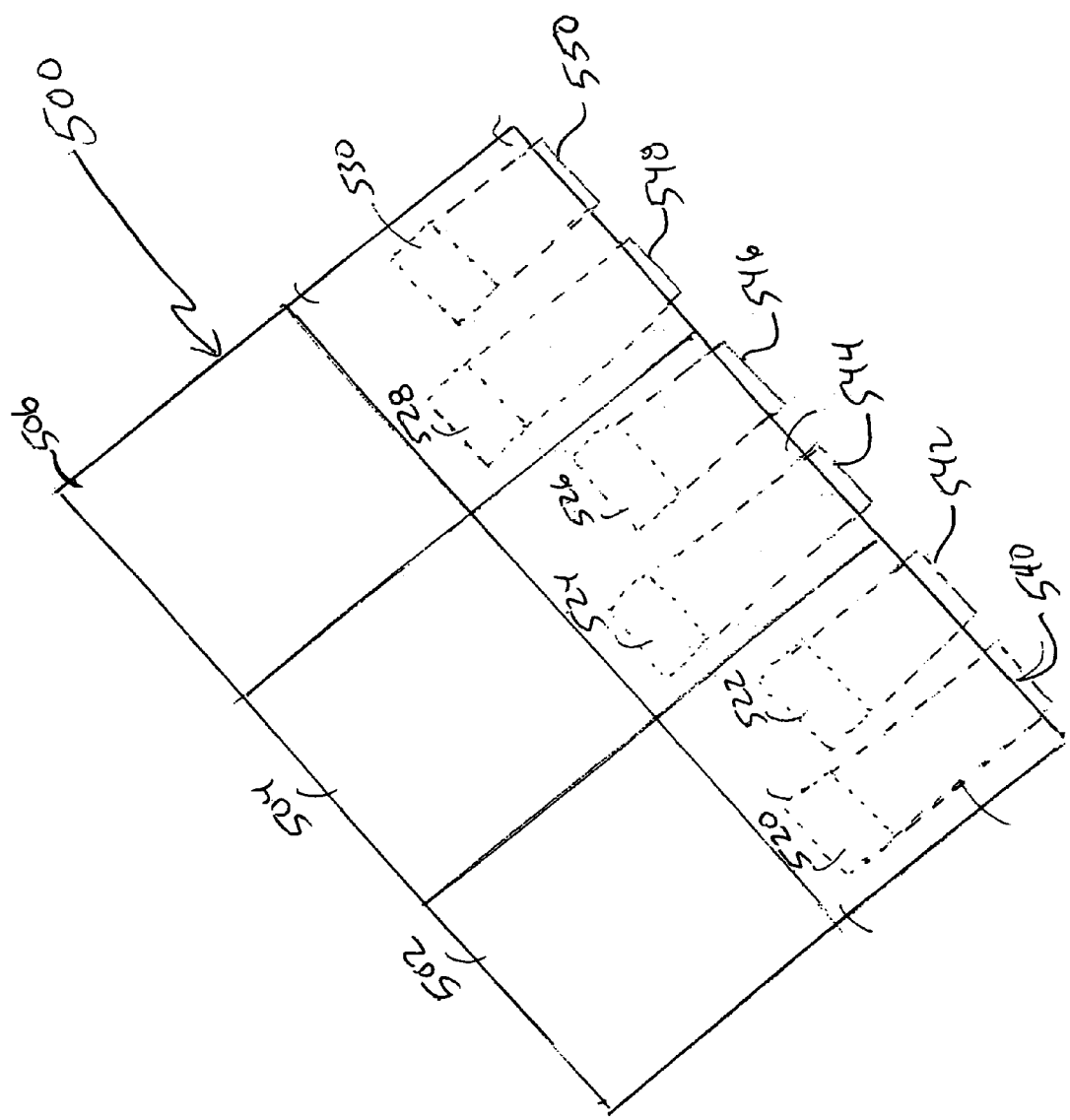

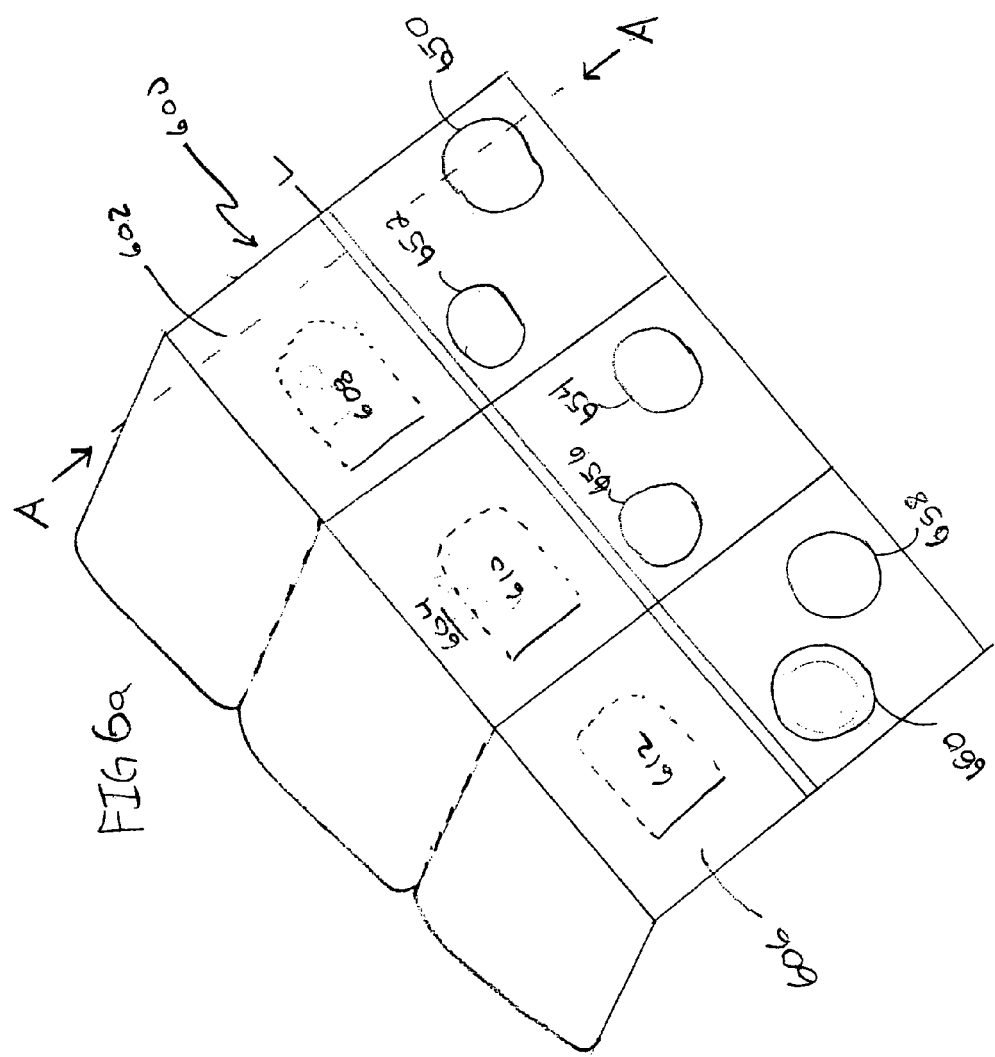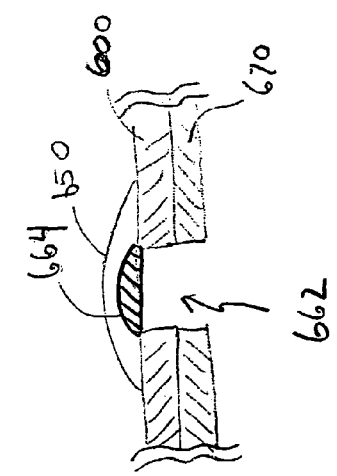

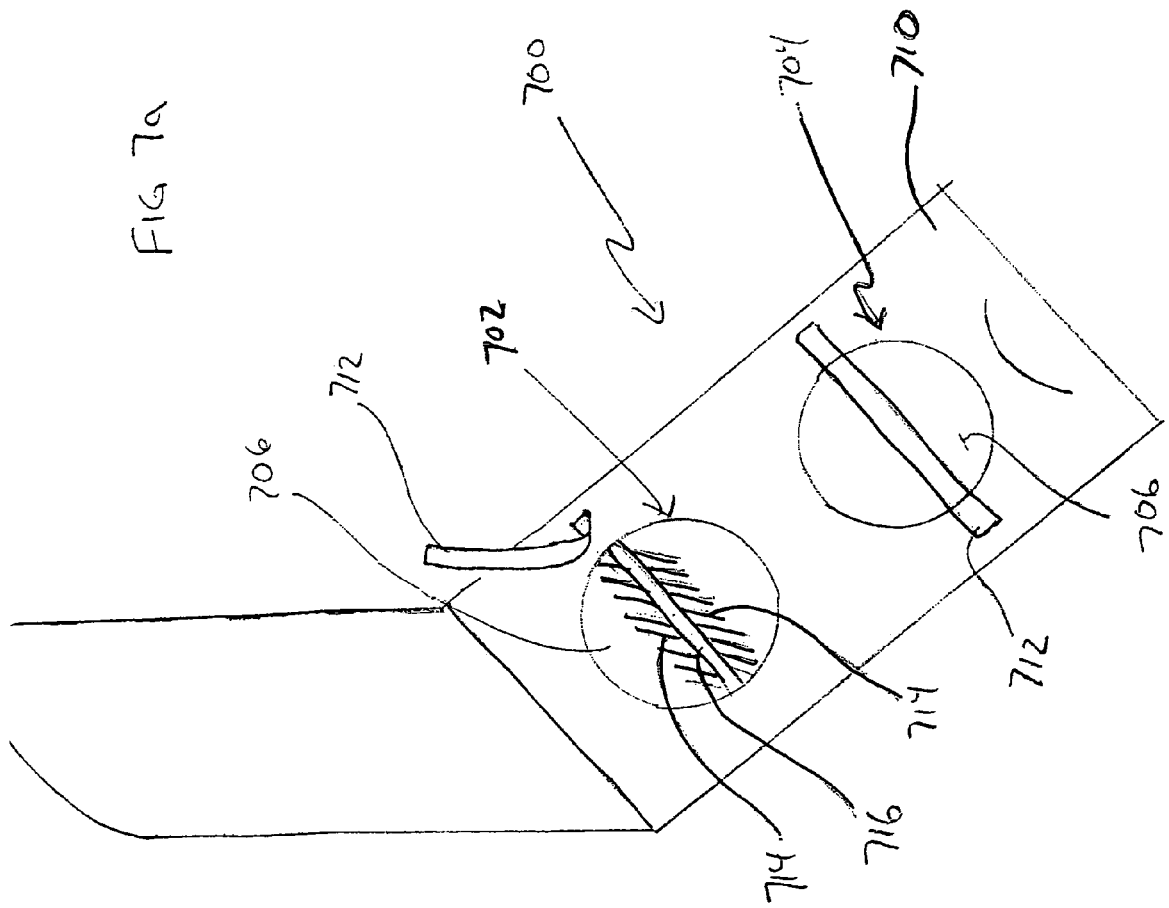

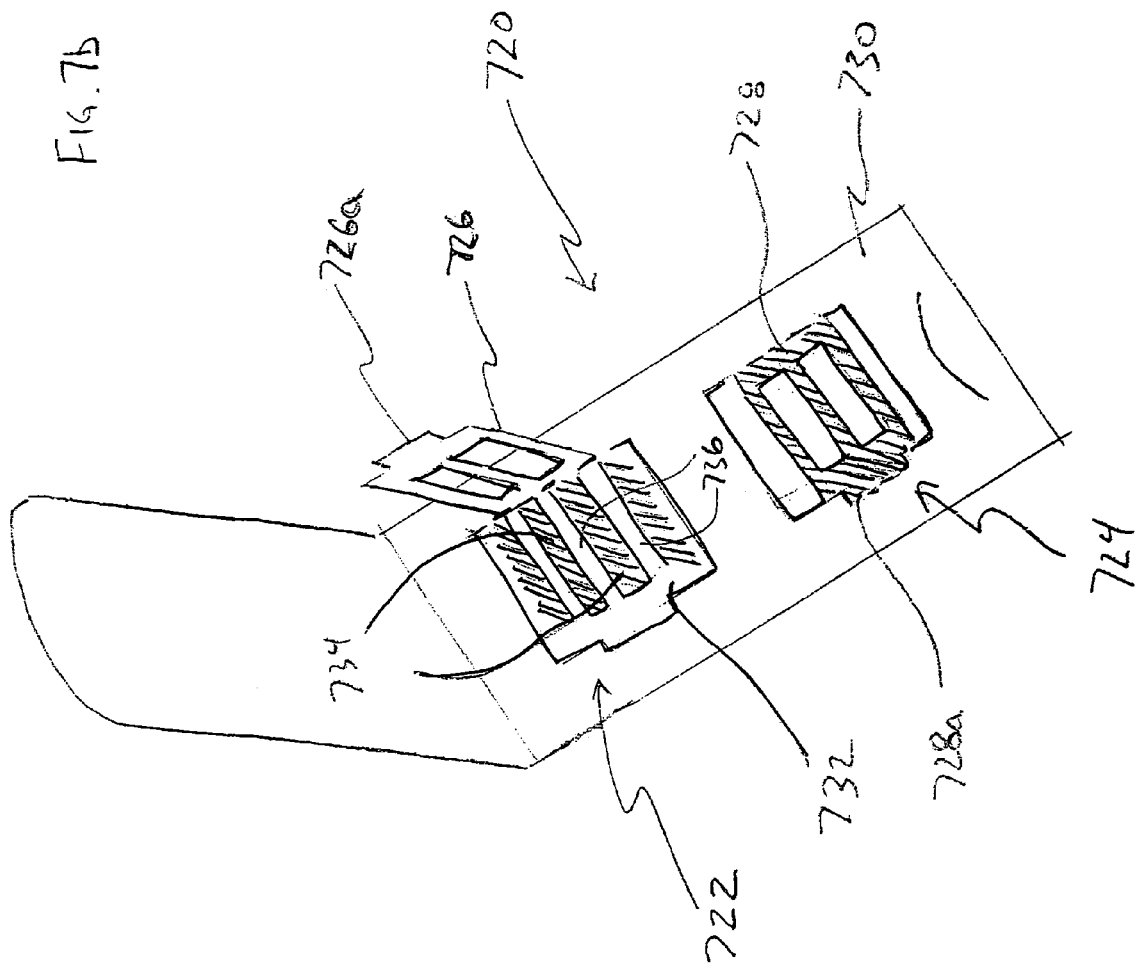

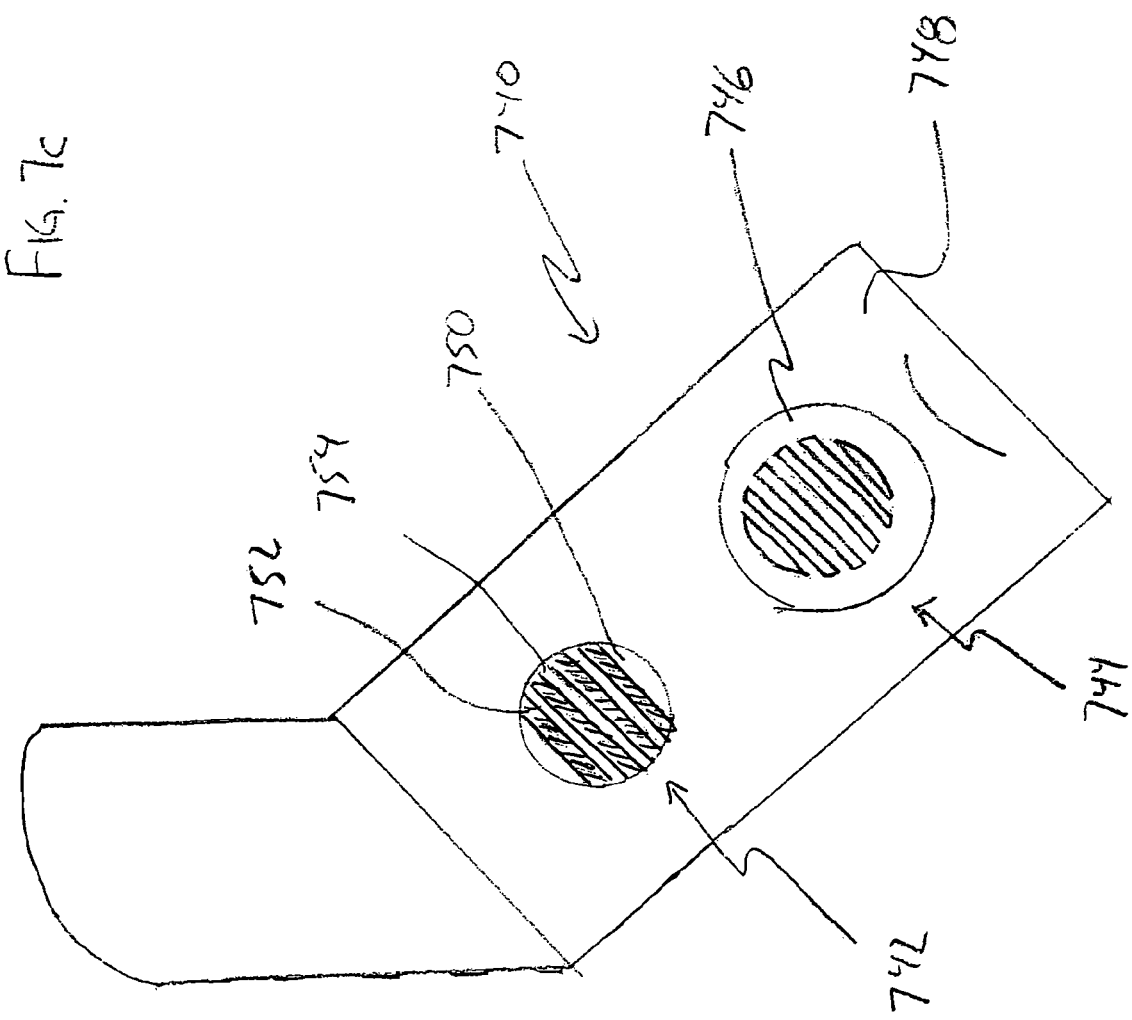

FECAL OCCULT BLOOD TESTING DEVICE AND METHOD

The present invention relates, generally, to a specimen collection device, including a device for collecting and determining the presence of occult blood in fecal matter, a method of testing using such a device and a test kit containing such a device.

BACKGROUND OF INVENTION

Over 100,000 persons per year in the U.S. are afflicted with cancer of the colon and rectum. When the number of colon/rectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90%. If, however, the disease is not detected until the later stages, the cure rate drops significantly. Thus, early detection of the disease is important to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Gross bleeding, however, is symptomatic of advanced cancers.

Digestive tract cancers in the early stages, including pre-cancerous polyps, also tend to bleed, giving rise to occult (hidden) blood in the fecal matter. Other pathological conditions, such as Crohn's disease and diverticulitis, can also give rise to the presence of occult blood in the fecal matter.

It is known that because of the relatively high fat content of fecal matter, blood, when present, is not distributed uniformly throughout it. For this reason, obtaining multiple samples from different areas of each bowel movement is desirable; but even a single positive test from any part of the feces should be considered a positive result.

Accordingly, test equipment and test procedures have been developed for use by physicians in testing for the presence of occult blood in fecal matter. One of the most successful tests is manufactured and sold by SmithKline Diagnostics of Sunnyvale, Calif. under the trademark HEMOCCULT and disclosed in Pagano U.S. Pat. No. 3,996,006, which is incorporated herein by reference in its entirety. In general, the Pagano test employs an absorbent paper impregnated with a guaiac reagent and encased in a special test slide having openable flaps on both sides of the test slide. To use the Pagano test slide, a sample of fecal matter is smeared onto the guaiac impregnated paper by opening the panel on one side of the test slide. Thereafter, the panel is closed. The panel on the opposite side of the test slide is then opened and a nonaqueous developing solution is applied to the guaiac impregnated paper. If occult blood is present in the fecal matter smeared on the opposite side of the paper, the guaiac reaction will dye the paper blue, providing a positive indication of the presence of blood in the fecal matter.

A drawback of this type of test is that a high percentage of false positives are obtained from patients who in fact do not have a cancer or other condition for which occult blood is symptomatic. For example, certain foods, such as rare red meat and peroxidase enzymes as present in certain foods, such as horseradish, broccoli and cantaloupe, can cause a false positive result.

To cut down on false positives, physicians place patients on specific diets designed to restrict the intake of animal proteins and other sources of false positives. Despite these efforts, large numbers of false positives still occur, as compliance with the restricted diet is unreliable. A false positive result in the test often results in expensive follow-up testing of patients who in fact have simply consumed a lot of meat or other undesirable foods just prior to the test.

A specific test for human hemoglobin has been devised. This test, offered by SmithKline Diagnostics under the tradename HEMESELECT, theoretically registers only human hemoglobin and not animal blood from meat or other agents, and therefore, theoretically does not require the patient to be on a special diet. While the hemoglobin test has the advantage over guaiac tests of registering only human hemoglobin, the hemoglobin test is expensive for a screening test and requires specially trained individuals to perform and read the test. Furthermore, hemoglobin tests are typically very sensitive, capable of detecting as little as 0.3 micrograms of blood, which is in excess of what a healthy normal person loses in fecal matter daily. Thus, because even healthy individuals lose a small amount of blood, which can be detected, a positive result may itself be a false positive leading to further costly, unnecessary test and procedures.

A need therefore exists for a relatively inexpensive test that has a minimal incidence of false positives and minimal manipulation of the specimen.

SUMMARY OF THE INVENTION

Embodiments of the present invention satisfy the foregoing, as well as other, needs. In accordance with one embodiment of the present invention, there is provided a specimen testing device comprising: a first panel comprising a first aperture for receiving a first specimen and a second aperture for receiving a second specimen; a second panel; a sheet disposed between the first and second panels for receiving at least the first specimen through the first aperture, wherein the sheet includes a test area having a reagent for possible reaction to the first specimen as part of a primary test procedure; and a removable tab at least partially aligned with the second aperture for receiving the second specimen, the removable tab accessible from an exterior of the device and available for use in a secondary test procedure.

In accordance with another embodiment of the present invention, there is provided a specimen testing device comprising: a first panel comprising a single aperture for receiving a first specimen and a second specimen from the single sample of a bowel movement smeared over the single aperture; a second panel; a sheet disposed between the first and second panels for receiving at least the first specimen through the single aperture, wherein the sheet includes a test area having a reagent for possible reaction to the first specimen as part of a primary test procedure; and a removable tab removable from an exterior surface of the first panel, the removable tab accessible from an exterior of the device and available for use in a secondary test procedure.

In accordance with another embodiment of the present invention, there is provided a method of testing for the presence of blood in fecal matter, the method comprising obtaining a primary specimen from a first area of the fecal matter on a testing device; obtaining a secondary specimen from the first area of the fecal matter on a removable tab of the testing device, wherein the secondary specimen is a portion of the primary specimen; testing the primary specimen for the presence of blood using a non-specific test; if the testing of the primary sample indicates the presence of blood, removing the removable tab, the removable tab having at least a portion of the secondary specimen; and testing the secondary specimen for the presence of blood using a specific test, wherein the testing of the secondary specimen facilitates either identification of a false positive result from the testing of the primary specimen with the non-specific test or confirmation of positive result from the testing of the primary specimen.

In yet another embodiment of the present invention there is provided a test kit including a specimen testing device described above; reagents for performing a primary test on specimens received into the first aperture of the first panel; and reagents for performing a secondary test on specimens received into the second aperture of the first panel.

In yet another embodiment, the device comprises a well for receiving a primary portion of a specimen. The device also includes a removable tab at least partially observing the well, the tab receiving a secondary portion of the specimen. The primary portion can be used in a primary test and the secondary portion can be used in a secondary test, the primary and secondary portions being deposited from a single smear of the specimen.

BRIEF DESCRIPTION OF THE DRAWINGS

The invention will now be described with reference to the accompanying drawings, in which:

FIG. 4 is a perspective view of the device of FIGS. 1 and 2 in an un-assembled state;

FIG. 5 is a perspective view of an absorbent sheet according to an alternate embodiment of the invention;

FIG. 6a is a perspective view of a device according to another embodiment of the invention showing the second panel containing circular tabs.

FIG. 6b is a sectional view of the second panel of FIG. 7a taken along line A-A showing the circular tab attached to the second panel.

FIGS. 7a-c are perspective views of alternate embodiments of the present invention utilizing the same well for both primary and secondary specimens.

DETAILED DESCRIPTION

Figure 1:
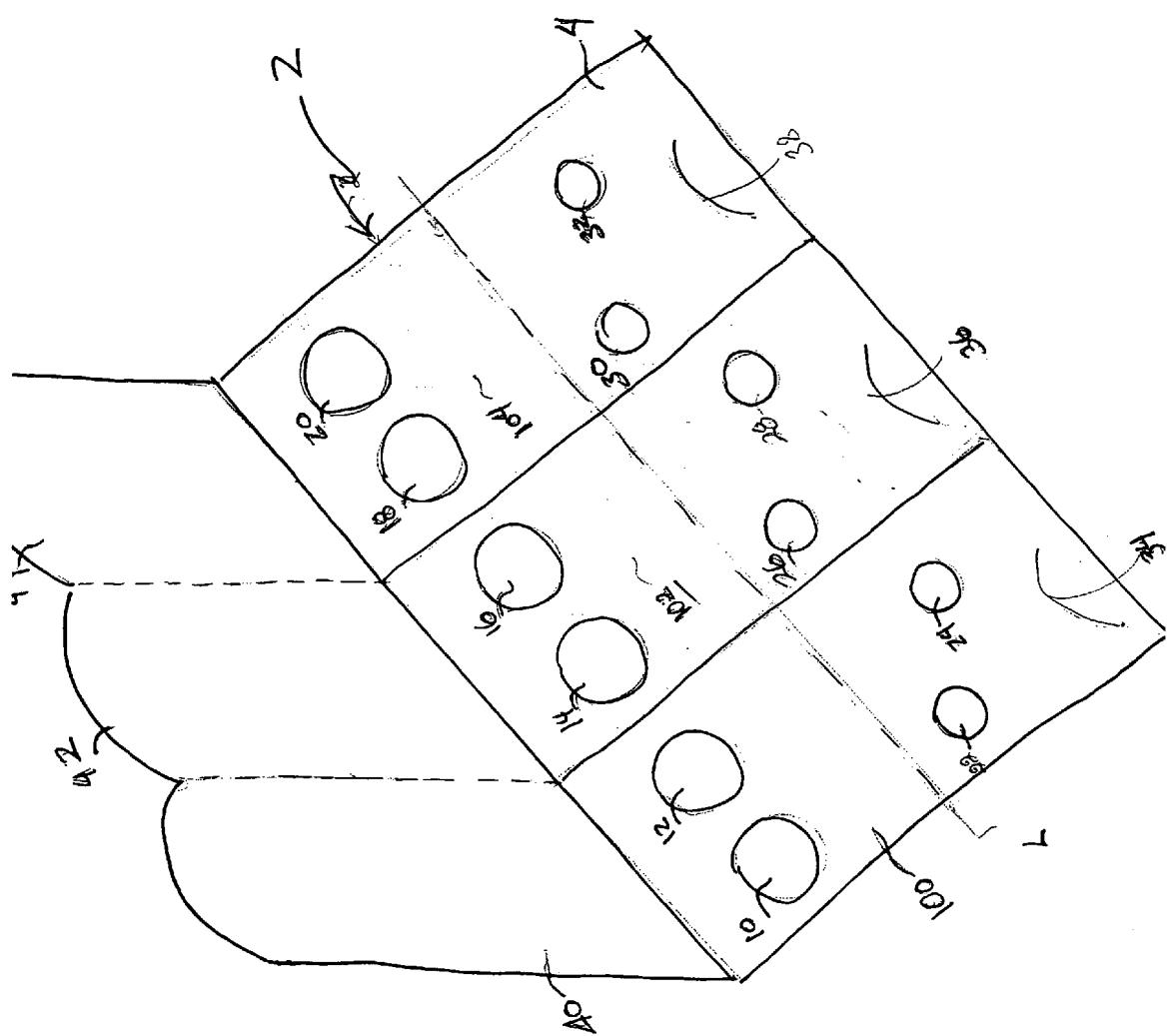
FIG. 1 is a front perspective view of a device according to one embodiment of the invention showing the first panel with three covers in the open position.

Referring to FIGS. 1-4, a fecal occult blood testing device 2 according to one embodiment of the invention, is shown. The device 2 generally includes three test areas 100, 102, 104 and is formed of a first panel 4 and a second panel 6, with an absorbent sheet 8 disposed between the first and second panels 4, 6, on which a specimen is placed.

Each test area, 100, 102, 104 is configured to receive both primary samples and secondary samples. The first test area 100 includes two apertures 10, 12 in panel 4 for receiving primary samples and two apertures 22, 24 for receiving secondary samples. Similarly, the second test area 102 includes apertures for primary samples 14, 16 and apertures for secondary samples 26, 28, and the third test area 104 includes primary 18, 20 and secondary 30, 32 sample apertures. According to the present embodiment, the shapes of the apertures on panel 4 can include, but are not limited to an oval, circle, square or rectangle.

Each of the three areas 100, 102, 104 also has a cover 40, 42, 44, respectively, thereto along a fold line extending transversely of the longitudinal axis L. Each cover 40, 42 and 44 is engageable with a corresponding flap formed by arcuate slit 34, 36, 38, respectively, which is used to maintain the covers in a closed position, after the samples are obtained.

Figure 2:
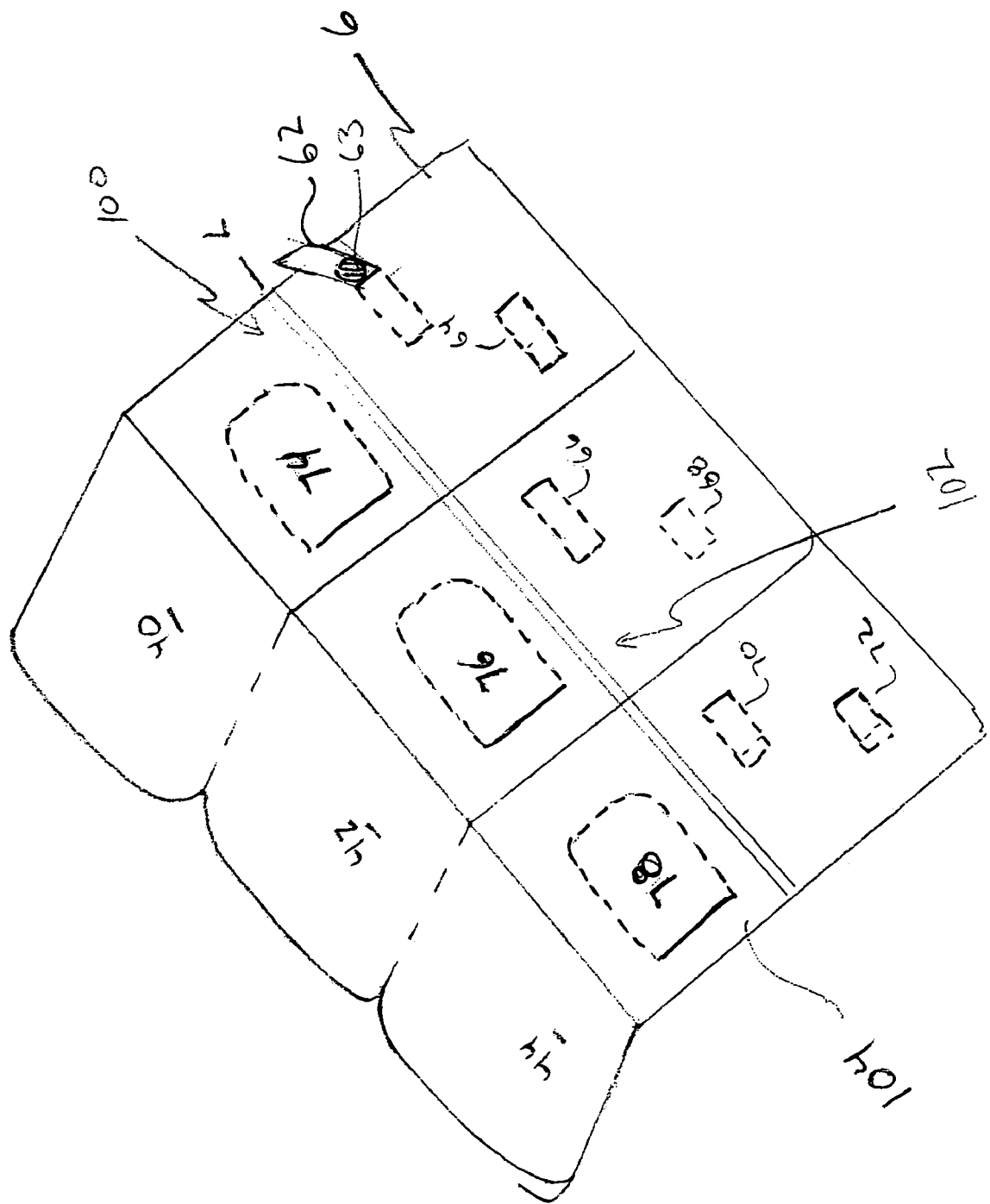
FIG. 2 is a rear perspective view of the device of FIG. 1 showing the second panel having one tab in an open position.

As shown in FIG. 2, each of the three test areas 100, 102 and 104 further includes, on the second panel 6, perforated tabs, each of which aligns with a corresponding aperture for a secondary sample. More specifically, test area 100 includes perforated tabs 62 and 64 aligned with apertures 22 and 24, respectively; in test area 102, tabs 66 and 68 align with apertures 26 and 28, respectively; and in test area 104, tabs 70 and 72 align with apertures 30 and 32, respectively.

Also shown in FIG. 2, in addition to the perforated tabs 62, 64, 66, 68, 70 and 72, each of which aligns with a corresponding aperture for a secondary sample, each test area 100, 102, 104 includes a flap which is aligned with the primary test area apertures of the first panel 4. More specifically, test area 100 includes a flap 74 aligned with both apertures 10 and 12 in such a way that opening of flap 74 exposes the primary test area of sheet 8, which is aligned with both apertures 10 and 12. Test area 102 includes a flap 76 aligned with both apertures 14 and 16 and test area 104 includes a flap 78 aligned with both apertures 18 and 20. As discussed below, the flaps 74, 76, 78 are opened to allow a reagent to be placed on the filter paper 8 when performing the non-specific test.

As described below, each tab 62, 64, 66, 68, 70 and 72 initially is maintained in a closed position, but may be opened along the perforations (in the present embodiment, along three sides although other configurations may be used) and separated from the second panel 6.

Figure 3:
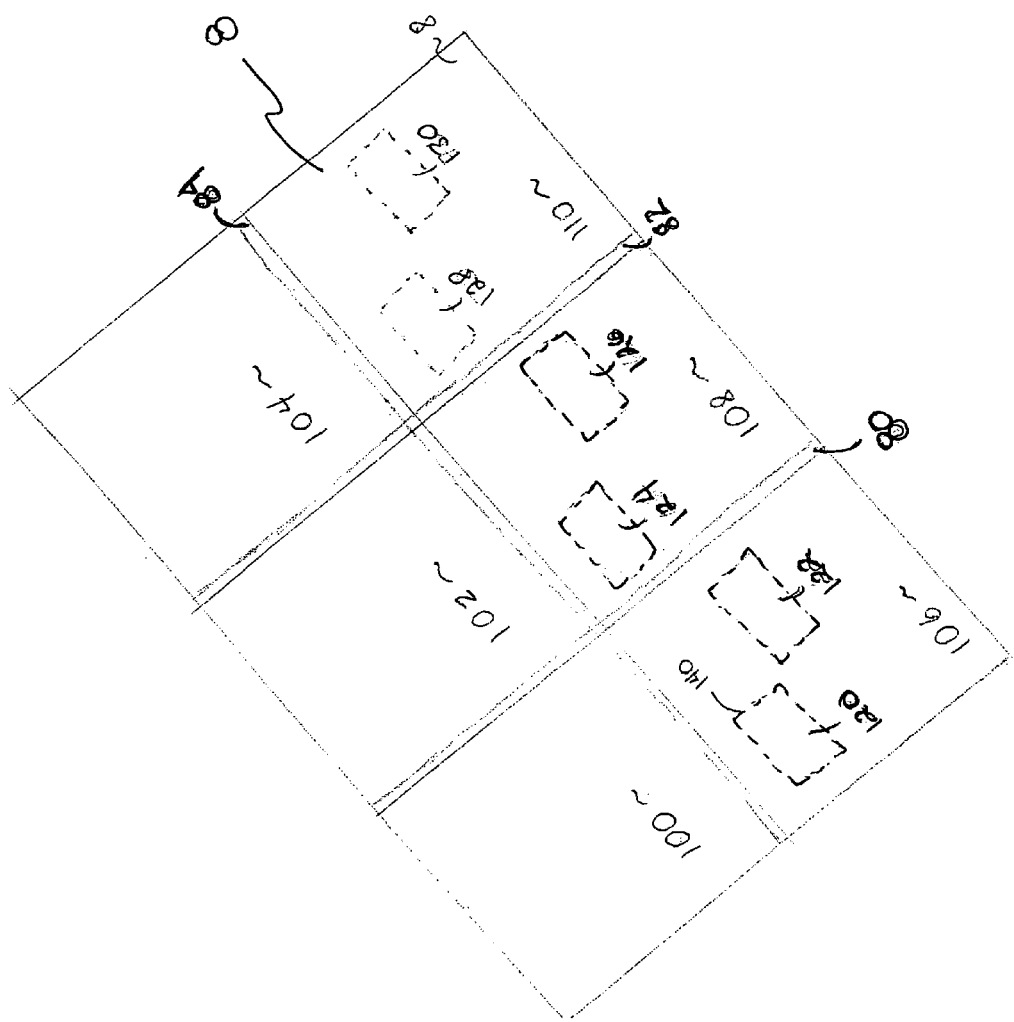
FIG. 3 is a perspective view of an absorbent sheet according to one embodiment of the present invention.

In the present embodiment, as illustrated in FIG. 3, the sheet 8 is a single piece of filter paper generally dimensioned as the second panel 6. In alternative embodiments, however, the sheet is dimensioned only to cover the primary sample apertures, where the sheet is impregnated with guaiac resin. Sheet 8 has six rectangular (although other shapes may be used) perforated zones 120, 122, 124, 126, 128 and 130, which, when the device 2 is assembled, are positioned in such a way as to align with and be between apertures 22, 24, 26, 28, 30 and 32, respectively, of panel 4 and tabs 62, 64, 66, 68, 70 and 72, respectively, of panel 6. Moreover, the zones 120, 122, 124, 126, 128 and 130 have perforations to enable the zones 120, 122, 124, 126, 128 and 130 to be removed from the sheet 8 along with the corresponding tabs 62, 64, 66, 68, 70 and 72, as described in more detail below. In alternate embodiments, the zones are not perforated, but rather simply tear away from the rest of the sheet.

Tabs 62, 64, 66, 68, 70 and 72 are aligned in such a way that the perforated zones 120, 122, 124, 126, 128 and 130 containing the specimens only come into contact with a portion of the tabs. The portion of the tab that does not come into contact with the specimen (e.g. 63) is used to pull the tab away from the device. In this way, physical contact between the tester and the specimen is prevented, thereby decreasing the chance of contamination of the specimen.

In certain embodiments, the tabs 62, 64, 66, 68, 70 and 72 have a spot of adhesive to allow the zones 120, 122, 124, 126, 128 and 130 to adhere thereto.

In certain embodiments, sheet 8 is made of an absorbent material, and is typically filter paper impregnated with a reagent which will react with hemoglobin components from blood and a peroxide solution to form a colored compound. Examples of suitable reagents are guaiac, tetraethyl benzidene, orthotoluidine and other similar chromogens. In the embodiment illustrated herein, the reagent impregnated in sheet 8 is guaiac. Here, the areas corresponding to the primary sample apertures 10, 12, 14, 16, 18 and 20 are impregnated with the reagent and the areas corresponding to the secondary sample apertures 22, 24, 26, 28, 30 and 32 are not impregnated with reagent. It is possible, however, for all sub-sections to be impregnated with reagent provided impregnation does not adversely affect any subsequent testing which might be conducted using the tab (secondary sample) areas.

To reduce risk of cross-contamination, prevent or minimize possible leakage of developing solution and to ease separation of the three test areas 100, 102, 104 on sheet 8, the test areas 100, 102, 104 are separated from each other by dividing regions 80 and 82, and the primary sample areas are separated from the secondary sample areas by dividing region 84, all of which may comprise a hydrophobic material, for example wax, glue or other suitable material. Alternatively, the primary sample area and the secondary sample area may be comprised of separate pieces of filter paper separated by a hydrophobic barrier. In still another embodiment, the samples are separated by a crimp or other physical barrier comprised of one or more of the panels themselves. As will be understood, the degree to which the areas are separated is dependent upon the tendency of the secondary testing procedure to be adversely affected by contamination.

As illustrated in FIG. 4, the panels 4, 6 and covers 40, 42, 44, can be formed of a single sheet of paper, cardboard or other suitable material, in which the apertures, slits, tabs and perforations are die-cut. The device 2 is assembled by overlaying panel 4 on to panel 6 with the sheet 8 therebetween. The assembly is held together with a suitable glue or adhesive. Although not required, to minimize sticking of the covers to the specimen, the panels 4 and 6 are provided on their inner surfaces with a layer of non-stick material, typically a wax layer although other materials may be used. In this way, the perforated zones 120, 122, 124, 126, 128 and 130 of sheet 8 carrying the secondary specimen can be removed without them sticking to the inner surfaces of the covers on the first and second panels.

The covers 40, 42 and 44 for first panel 4 may be provided with appropriate printed matter to assist the patient, physician and/or laboratory. For example, the patient's name, address and instructions on how to use the device may be printed on the covers 40, 42 and 44. Such instructions may include instructing the patient to apply a specimen from the same areas of the fecal matter, or even the same smear, in each of the primary sample well and corresponding sample well. Blood is not uniformly distributed throughout the fecal matter because of the high fat content of the fecal matter. As discussed below, using the same sample in both the primary and secondary sample wells accounts for this and allows the secondary specimen to be used in a confirmatory testing procedure. Other printed matter that may also be provided on the first panel 4 includes for example, the sample number and the test to be performed (e.g., primary analysis or secondary analysis). Printed matter may also be provided on the second panel 6. For example, instructions to the doctor as to how to carry out testing by opening any flaps and/or tabs on second panel may be provided.

In a further embodiment, panel 4 can be provided with indicating means for locating where specimen is to be placed on the sheet. The indicating means may comprise printed circles or other shapes on the panel as a visible indicator to the user of where to place the specimen.

FIG. 5 shows the absorbent sheet 500 according to an alternate embodiment of the device of the invention suitable for use with the panel 4 of the prior embodiment. Sheet 500 includes test areas 502, 504 and 506. Each test area 502, 504 and 506 of Sheet 500 contains two perforated zones, one corresponding to each of the secondary sample apertures: test area 502 contains perforated zones 520 and 522; test area 504 contains perforated zones 524 and 526; and test area 506 contains perforated zones 528 and 530. Each perforate zone 520, 522, 524, 526, 528 and 530 is adhered to a corresponding tab 540, 542, 544, 546, 548 and 550, respectively. In other words, each perforated zone is backed by the tab—another layer, such as paper, cardboard, plastic or other material—which extends beyond the bottom edge where the first panel meets the second panel, through a corresponding opening or slot. Each tab can be used to pull the corresponding perforated zone from between the panels to be used for the secondary test procedure (e.g., immunochemistry test). As such, in this embodiment, there is no need for any tabs in the secondary test areas of the second panel; instead, the sample can be removed from the device simply by pulling the appropriate pull-tab. In alternate embodiments, the pull tab may comprise a lengthened section of the sheet without any backing.

FIG. 6a and FIG. 6b show a second panel 600 with test areas 602, 604 and 606 according to another embodiment of the invention. Although not shown, the present embodiment uses a front panel as shown in FIG. 2 As such, flaps 608, 610, 612 are aligned with primary sample apertures in the front panel for opening during the primary test procedure. Furthermore, each circular (although other shapes may be used) tab 650, 652, 654, 656, 658 and 660 is aligned with a corresponding aperture on the front panel 670 for a secondary specimen. There are corresponding apertures in panel 600 located opposite of the secondary specimen apertures of the front panel 670, which apertures are covered by circular tabs 650, 652, 654, 656, 658 and 660. The circular tabs are removably adhered to the rear or outside surface of panel 600 via an adhesive located along all or part of the circumference or edge of each tab. In this embodiment, there is no sheet located between the panels in the secondary test area, however, the center of each tab 650, 652, 654, 656, 658, 666 includes a piece of the sheet adhered thereto for receiving the secondary sample, although the sheet is not required.

As shown in the sectional view of FIG. 6b, the aperture 662 in panel 600 is covered by tab 650, which includes a piece of sheet 664 aligned with the aperture 662. The center of the circular tabs receive the secondary specimen through the secondary apertures of panel 670 and apertures 662 of panel 600. The circular tabs and their corresponding specimens can be removed from the device by peeling them off of the device. In certain embodiments, the tabs are dimensioned to fit within a test tube or other container used with a secondary, specific test procedure.

With regard to the embodiment of FIGS. 1-4, where a fecal sample is to be analyzed, the device 2 is typically sent home with a patient. The patient opens the cover 40 on the first panel 4 of the device and smears a first fecal specimen through one primary aperture 10 and also through the corresponding secondary aperture 22, thereby depositing samples on the exposed sheet 8. In the present embodiment, a primary sample aperture and a secondary sample aperture are identified through markings on the first panel, namely, for receiving sample from the same area or region of the bowel movement being tested. A second fecal specimen, for example, taken at a different time as a result of a different bowel movement or from a different region of the same bowel movement as the first specimen, is then smeared through other corresponding primary 12 and secondary sample 24 apertures, onto the exposed sheet 8. With the samples taken, the cover 40 is closed and secured in the arcuate slit 34. It should be noted that each of the secondary samples taken is received (or deposited on), at least partially, by a corresponding perforated zone. In embodiments where the sheet 8 does not extend to the region corresponding to the secondary sample apertures, the secondary sample is received by a portion of the corresponding tab.

The patient obtains the requisite number of samples and typically either returns the device to the physician or to a laboratory.

To conduct a primary (e.g., non-specific) analysis, the flap 74 on second panel 6 covering the primary aperture wells of the first test area 100 in which the specimens have been applied, is opened and developer solution is applied to the exposed sheet 8.

Typically, if both primary specimens test negative, no further testing is required, thereby saving the cost of a secondary analysis. If a primary specimen tests positive, a secondary analysis can be performed. More specifically, to perform a secondary analysis, the tab (by way of example, 62) corresponding to the "positive" primary sample aperture (e.g., 10) is opened, thereby tearing the corresponding perforated zone (e.g., 120) away from sheet 8. The perforated zone 120 carrying the secondary sample is removed from device 2 by tearing the tab 62 from the second panel 6. The tab 62, along with the perforated zone 120, is placed in a container or tube for secondary analysis. In the present embodiment, the secondary analysis is an immunochemical test, which has fewer false positives than the primary test, the guaiac test. As such, because the secondary sample corresponds to the positive primary sample (e.g., is preferably a portion of the same specimen as the primary specimen) the secondary analysis can facilitate confirmation of the positive primary test or indicate that the primary test was a false positive, thereby combining the sensitivity of the primary test with the specificity of the secondary test.

In the alternate embodiment of FIG. 5, once the primary analysis has been performed, as above, and a positive result is obtained, a secondary analysis is similarly performed by pulling the pull-tab corresponding to the positive primary sample from the device and placing the pull-tab, along with the secondary sample, in a container or otherwise using it for further testing.

Various alternate embodiments in which the removable tab is placed on the first panel and in which the aperture for receiving the primary sample is the same aperture used for receiving a secondary sample will not be described with reference to FIGS. 7a-c. It should be appreciated that by using the same aperture or well for both the primary and secondary specimen, portions of the same specimen (i.e., a sample from the same region of a bowel movement) is used in both the primary and corresponding secondary test procedures. This is beneficial given the tendency of the blood to be dispersed (if present) non-uniformly through a bowel movement. As an initial matter, it is to be understood that although a single test area is shown in each figure, multiple test areas may be combined into a single device.

Turning first to FIG. 7a, there is shown a device 700 having two wells 702, 704 for receiving samples. Although not shown, the device 700 is constructed generally as the embodiment of FIG. 4, having a sheet 706 between a first panel 710 and a second panel (not shown). Apertures in the first panel 710 define the wells 702, 704.

Each well 702, 704 is partially covered by a tab 712 in the form of a strip, such as a metal, plastic, wax coated, impervious paper or other material. The tab 712 is removable, either by using removable adhesive to attach it to the first panel 710 or, as in FIG. 7b, by using perforations other means allowing the tab to be torn away.

In use, a patient smears a specimen in a well 702, thus causing the sample to be placed on the sheet 706 as well as on the tab 712. Accordingly, the well 702 includes areas both containing the specimen 714, as well as areas without the specimen 716. Notably, the primary specimen on the sheet 706 and secondary specimen on the tab are necessarily from the same smear.

When performing the primary test procedures, the physician or laboratory proceeds generally as described above, by opening a flap on the rear of the device and applying developing solution. In the event the primary test is positive, the tab 712 may be removed and used in connection a secondary testing procedure. The tab 712 may be removed prior to depositing the developing solution, (for example, to help prevent contamination). Additionally, the tab 712 extends beyond the aperture, thereby providing a means for easy removal, without contamination of the sample.

In certain embodiments in which the primary sample and secondary sample are obtained in the same well with a tab covering a portion of the well (as in FIGS. 7a-c), it is possible to apply the developing solution in connection with the primary test directly to the front of the device, through the aperture in the first panel. In such embodiments, the tab or tabs are first removed, thereby exposing areas of the sheet with and without the specimen. Because the tab or tabs provide a metering effect (as also shown in FIGS. 7b and 7c), controlling the amount of specimen in the well and on the sheet, the physician or laboratory is able to read the results of the test without the need for a flap on the rear of the device. Even where a rear flap is used, the metering effect is desirable, as the test results are easier to read.

Moreover, it should be understood that the tab or even non-removable covering may be used to meter the amount of specimen in any of the embodiments described herein. In certain embodiments the metering cover is integrally formed with the first panel and is not removable, serving only a metering purpose and not as a means for collecting a secondary specimen.

In other alternate embodiments, the tab may not be placed on the first panel, but may be placed under it, between the first panel and the sheet.

In the embodiment of FIG. 7b, the device 720 similarly includes two wells 722, 724, each for receiving both primary and secondary samples. In the present embodiment, however, rather than using a tab formed of a strip adhered to the surface of the first panel, the present tabs 726, 728 are formed by punching out portions of the first panel 730. Preferably, each tab 726, 728 includes an extension 726a, 728a or other portion extending away from the area receiving the specimen, thereby providing the tester an area for grasping the tab 726, 728 for easy removal without contaminating the specimen.

As shown in connection with the first well 722, in which the tab 726 is in an open position, placing the sample in the well 722 results in a pattern on the sheet 732 of areas with specimen 734 and areas without the specimen 736. Again, a single smear results in both the primary and secondary specimens, thereby ensuring the two specimens are taken from the same portion of a sample. Indeed, the secondary specimen is actually a portion of the primary specimen.

In use, the primary test may be performed either by opening a flap on the rear of the device 720, and depositing the developing solution in the well 722, 724, either before or after removing the tab 726, 728. Alternatively, the tab 726, 728 can be opened and developing solution placed directly in the well 722, 724. Upon a positive primary specimen, the corresponding tab 726, 728 may be used in connection with a secondary test to confirm a positive result or to identify a false positive result.

FIG. 7c illustrates another exemplary embodiment in which the same well (and smear) is used for both the primary and secondary samples and, accordingly in which specimens from the same portion of a bowel movement are used for both the primary and secondary test procedures. More specifically, the device 740 includes two wells 742, 744. Prior to use, each well 742, 744 is covered with a tab 746 with a plurality of openings, which is adhered to the surface of the first panel 748 by removable adhesive. (Well 742 is shown after use, with the corresponding tab removed.) In the present embodiment, the tab 746 is wider than the well 744 to provide an area without specimen for grasping. In other embodiments, the tab can include an extension for ease of grasping.

In use, the patient smears the specimen in the wells 742, 744 across the tabs 746, thereby depositing some specimen in the well on sheet 750 and some specimen on the tab 746. As shown in the first well 742, in which the tab has been removed, the tab meters the amount of specimen in the well 742, thus resulting in a pattern of areas both with 752 and without 754 specimen.

As with the embodiments of FIGS. 7a and 7b, the primary test procedure may be carried out via a flap on the back of the device 740 or by depositing developing solution directly into the well after removing the corresponding tab. Because the tab provides a metering function, the results of a the primary test may be read without the need for the flap on the rear. In the event the primary test is positive, the corresponding tab may be used to perform the secondary test procedure.

According to an additional embodiment, the testing device may be provided individually or may be packaged in kit form. For example, kits might be prepared comprising numerous testing devices, reagents required to perform the primary analysis for such devices, such as the developing solution used in the guaiac test, sample tubes in which to place the tabs and perforated zones from the sheet and materials for a secondary test, such as, but not limited to, a specific immunochemical test, such as an ELISA, Lateral Flow Device, or any testing procedure used for human blood.

The test tubes may be pre-filled with the test reagents or they may be provided separately. To reduce costs, the kit may contain fewer immunochemical test reagents than primary test reagents given the use of the immunochemical test in a confirmatory role.

Embodiments of the present invention enjoy numerous advantages. For example, the device can be embodied in one card which readily facilitates transference between the doctor and the patient and between the doctor and another testing location, such as a laboratory. The device is easy to use by the patient and is inexpensive to produce. One further advantage is that the device allows a first test to be carried out and, in the event that a specimen is positive, subsequent testing can be carried out on a separate portion of the same specimen. In addition, the device is such that it reduces the possibility of contamination of the secondary sample when being removed from the device.

Those skilled in the art will recognize that the method and system of the present invention has many applications, may be implemented in many manners and, as such, is not to be limited by the foregoing exemplary embodiments and examples. In this regard, any number of the features of the different embodiments described herein may be combined into one single embodiment, and all features of a given embodiment need not be included in other embodiments. Moreover, the scope of the present invention covers conventionally known and future developed variations and modifications to the components and materials described herein, as would be understood by those skilled in the art.

For example, in the above description, the apertures, perforated zones and tabs are illustrated as rectangular or circular. However, any desired shape may be used, for example oval, square, rectangular or other polygon.

In the above description, the tabs are illustrated as being perforated on three sides. However, the tabs may also be perforated on fewer sides, (e.g., two sides, with a cut-out along, one side) or on all sides and be punched out of the device for use in the secondary analysis of the specimens. Tabs may also be oriented in different directions.

Furthermore, although embodiments are shown with three test areas for testing three bowel movements, with two specimens from each, other numbers of specimens may be taken.

The embodiments of the invention has been described with reference to analysis of fecal samples for stool occult blood. However, the device may be used for screening and testing of other biological specimens, for example blood and AIDS tests, urine tests and pregnancy tests.

While the present invention has been described in considerable detail, the invention disclosed herein is not limited to the detailed description, and is to be afforded the full scope of the appended claims and all equivalents thereto.

What is claimed is:

1. A method of testing for the presence of blood in fecal matter using a testing device having:
   a first panel having a first aperture for receiving a first specimen and a second aperture for receiving a second specimen and forming a first exterior surface of the device;
   a second panel opposite the first panel and forming a second exterior surface of the device;
   a sheet disposed between the first and second panels for receiving at least the first specimen through the first aperture, wherein the sheet includes a test area having a reagent for possible reaction to the first specimen as part of a primary test procedure; and
   a reagent-free removable tab, integrally formed from the second panel, the removable tab being a portion of the second panel and forming a part of the second exterior surface and accessible from an exterior of the device, the tab having a first portion, which is aligned with the second aperture on the first panel for receiving the second specimen and available for use in a secondary test procedure and a specimen-free second portion, which is not aligned with any aperture on the first panel and which comprises a specimen-free grasping area,
   the method comprising:
   obtaining a primary specimen from a first area of the fecal matter via the first aperture on the testing device;
   obtaining a secondary specimen from the first area of the fecal matter via the second aperture on the first portion of the removable tab of the testing device;
   testing the primary specimen for the presence of blood using a non-specific test;
   if the testing of the primary sample indicates the presence of blood, removing the removable tab by pulling the specimen-free grasping area of the second portion of the removable tab such that the removable tab is separated from the testing device, the first portion of the removable tab having at least a portion of the secondary specimen; and
   testing the secondary specimen for the presence of blood using a specific test, wherein the testing of the secondary specimen occurs once the removable tab is removed from the testing device and facilitates either identification of a false positive result from the testing of the primary specimen with the non-specific test or confirmation of positive result from the testing of the primary specimen.

2. The method of testing according to claim 1, wherein the non-specific test is a guaiac test.

3. The method of testing according to claim 1, wherein the specific test is an immunochemical test.

4. The method of claim 1, wherein the primary specimen is obtained in a well on the device and the removable tab partially obscures the well, the testing the primary sample comprising providing a solution through a flap on the second panel of the device.

5. The method of claim 1, wherein the primary specimen is obtained in a well on the device and the removable tab partially obscures the well, the testing the primary sample comprising removing the tab and providing a solution into the well.

6. The method of claim 1, wherein the primary specimen is obtained in a first well formed by a first aperture in a front panel of the device and the secondary specimen is obtained in a second well formed by a second aperture in the front panel in the device.

7. The method of claim 1, wherein the primary specimen is obtained in a first well formed by a first aperture in a front panel of the device and the secondary specimen is obtained in a second well formed by a second aperture in the front panel in the device, the removable tab removably adhered to a rear panel of the device and aligned with the second well, the removing of the tab comprising removing the tab from the rear panel.

8. The method of claim 1, wherein the removable tab is dimensioned to fit in a container and wherein testing of the secondary specimen includes placing the removable tab having a portion of the secondary specimen in the container.

9. A specimen testing device comprising:
a first panel having a first aperture for receiving a first specimen and a second aperture for receiving a second specimen and forming a first exterior surface of the device;
a second panel opposite the first panel and forming a second exterior surface of the device;
a sheet disposed between the first and second panels, the sheet including a test area aligned with the first aperture such that depositing the first specimen through the first aperture deposits the first specimen directly on the test area, and having a reagent for possible reaction to the first specimen as part of a primary test procedure; and
a reagent-free removable tab, integrally formed from the second panel, the removable tab being a portion of the second panel and forming a part of the second exterior surface and accessible from an exterior of the device, the tab having a first portion and a second portion,
wherein the first portion is aligned with the second aperture on the first panel and constructed such that depositing the second specimen through the second aperture causes the second specimen to be directly deposited on the first portion of the tab to be made available for use in a secondary test procedure which is performed once the removable tab is removed from the testing device; and
wherein the second portion is not aligned with the second aperture and is constructed such that depositing the second specimen through the second aperture does not deposit the second specimen on the second portion, and which comprises a specimen-free grasping area for removing the tab.

10. The device according to claim 9, wherein the first aperture is different from the second aperture.

11. The device according to claim 9, wherein the tab includes material for receiving the second specimen.

12. The device according to claim 9, wherein the first aperture and the second aperture are a single aperture and the first portion of the tab is aligned with a portion of the single aperture, the first specimen and second specimen thus being from a single sample of a bowel movement smeared over the single aperture.

13. The device according to claim 9, wherein the first and second panels have printed matter thereon indicating that the first specimen and second specimen should be from a like region of a bowel movement, thereby facilitating the second specimen to be used as a confirmatory specimen.

14. The device according to claim 9, wherein the removable tab comprises a removable portion of the sheet.

15. The device according to claim 9, wherein the first panel includes multiple first apertures for receiving multiple first specimens and multiple second apertures for receiving multiple second specimens.

16. The device according to claim 9, further comprising a cover for covering the first panel.

17. The device according to claim 9, wherein the first panel and second panel are formed from a single piece of material and are hingedly connected to each other.

* * * * *